United States Patent [19]
Waldrep et al.

[11] Patent Number: 5,958,378
[45] Date of Patent: Sep. 28, 1999

[54] HIGH DOSE LIPOSOMAL AEROSOL FORMULATIONS CONTAINING CYCLOSPORIN A OR BUDESONIDE

[75] Inventors: J. Clifford Waldrep, The Woodlands; Vernon Knight, Houston; Melanie B. Black, The Woodlands, all of Tex.

[73] Assignee: Research Development Foundation, Carson City, Nev.

[21] Appl. No.: 08/731,605

[22] Filed: Oct. 16, 1996

Related U.S. Application Data

[63] Continuation-in-part of application No. 08/675,654, Jul. 3, 1996, abandoned.

[51] Int. Cl.$^6$ .............................. A61K 9/12; A61K 9/127
[52] U.S. Cl. .............................................. 424/45; 424/450
[58] Field of Search ........................................ 424/45, 450

[56] References Cited

PUBLICATIONS

Waldrep et al. (1993). Int. J. Pharmaceutics 97:205–212.
Manthous et al. (1994). Chest 106(2):560.
Fornhem, C. (1995). Dis. Abst. Int., vol. 57/02–C, p. 549.

*Primary Examiner*—Raj Bawa
*Attorney, Agent, or Firm*—Bejamin Aaron Adler

[57] ABSTRACT

The present invention provides a high dose pharmaceutical liposome aerosol composition comprising about 12–30 mg/ml of a pharmaceutical compound, and about 130–375 mg of a phospholipid/ml starting reservoir concentration. Specifically, the present invention is drawn to anti-inflammatory glucocorticoids, immunosuppressive compounds, anti-fungal compounds, antibiotic compounds, anti-viral compounds, and anti-cancer compounds delivered via a high dose liposome aerosol composition in a phospholipid. More specifically, the invention provides a high dose cyclosporin A liposome aerosol composition comprising up to about 30 mg/ml cyclosporin A in up to about 225 mg of a phospholipid/ml starting reservoir concentration. Also provided is a high dose budesonide-liposome aerosol composition comprising up to about 15 mg/ml budesonide in up to about 225 mg of a phospholipid/ml starting reservoir concentration.

15 Claims, 8 Drawing Sheets

HIGH DOSE LIPOSOMAL AEROSOL FORMULATIONS CONTAINING CYCLOSPORIN A OR BUDESONIDE

This application is a continuation-in-part of U.S. Ser. No. 08/675,654, filed Jul. 3, 1996, now abandoned.

BACKGROUND OF THE INVENTION

1. Field of the Invention

The present invention relates generally to the fields of biochemical pharmacology and medicinal chemistry. More specifically, the present invention relates to high dose liposomal aerosol formulations of various pharmaceuticals, including cyclosporin A and budesonide.

2. Description of the Related Art

In the lung, many different diseases have been treated successfully through utilization of aerosol delivery systems used to deposit drugs directly on to the pulmonary surfaces. For delivery in this manner, a variety of devices have been developed (for example, metered dose inhalers and dry powdered inhalers). Jet-nebulizers have been used clinically for aerosol delivery of water soluble drugs and micronized suspensions; however, their use with water insoluble, hydrophobic compounds has been limited.

The development of liposomal formulations compatible with aerosol delivery has allowed the jet nebulizer to deliver additional drugs. Utilization of liposomes for aerosol delivery has many advantages, including aqueous compatibility; sustained pulmonary release allowing maintanence therapeutic drug levels, and, further, liposomes facilitate intracellular delivery, particularly to alveolar macrophages.

The efficacy of localized, topical therapy via aerosols is determined by the amount of drug delivered at the sites of disease within the lung; and there are several different key parameters that determine the amount of delivery, thus, the therapeutic efficacy of aerosol formulations. For example, nebulizer design and variation, operating conditions (e.g., flow rate), and the presence of ancillary equipment (tubing, connectors, mouth pieces, face masks, and the like), are important variables. Thus, aerosol output efficiency can be increased through proper implementation of the proper nebulizer device. Inappropriate implementation of the device and/or imperfect parameters can affect inhaled dosages, delivery sites and influence the therapeutic outcome.

Drug formulation also is a critical factor regulating aerosol output efficiency and aerodynamic properties of drug-liposomes. It has been discovered that drug-liposome output efficiency can be increased through the utilization of liposomes formulated with low phase transition temperatures (see Waldrep et al., *J. of Aerosol Med.* 7:1994 (1994) and Waldrep et al., *Int'l J. of Pharmaceutics* 97:205–12 (1993)). An additional method to increase aerosol drug-liposome output is to increase the drug and phospholipid reservoir concentrations. Nebulization of some drug-liposome formulations at greater than 50 mg/ml results in clogging of the nebulizer jets; yet empty liposomal formulations up to 150 mg/ml have been successfully nebulized (see Thomas, et al., *Chest* 99:1268–70 (1991)). Further, the aerosol performance (output and particle size) is influenced in part by physiochemical properties such as viscosity and surface tension. Such variables affect the maximal drug-liposome concentrations compatible with aerosol delivery via the jet nebulizer.

Anti-inflammatory glucocorticoids have been used for the treatment of asthma and other severe inflammatory lung diseases for over forty years. More recently, aerosol glucocorticoid therapy has been used increasingly as a route of administration. Presently, there are several different, though structurally similar, topically active glucocorticoids—e.g., beclomethasone, budesonide, flunisolide, triamcinolone acetonide and dexamethasone—that are available in metered dose inhalers or dry powder inhalers for aerosol treatment of asthma and other inflammatory diseases of the lung. While systemic complications such as suppression of the hypothalamic-pituitary axis, cataract formation and growth inhibition are infrequent in asthmatics treated with inhaled glucocorticoids, localized side effects of candidiasis and dysphonia are more common, necessitating the use of accessory spacer devices. At present in the United States, there are no glucocorticoid formulations approved for nebulized administration, although micronized suspensions of beclomethasone and budesonide are employed in Europe and Canada.

The present invention is drawn to concentrated, high dose cyclosporin-A-liposome and budesonide-liposome aerosol formulations that provide maximal aerosol output with particle size ranges within the optimal range of 1–3 μm mass median aerodynamic diameter (MMAD). The prior art is deficient in such liposomal aerosol formulations. The present invention fulfills this long-standing need and desire in the art.

SUMMARY OF THE INVENTION

The object of the present invention is to provide a high dose pharmaceutical liposome aerosol composition comprising about 12–30 mg/ml of a pharmaceutical compound, and about 130–375 mg of a phospholipid/ml starting reservoir concentration. in one embodiment of the present invention, there is provided a high dose pharmaceutical compound-liposome aerosol composition comprising about 12–30 mg/ml of the pharmaceutical compound in up to about 130–375 mg of a phospholipid/ml starting reservoir concentration, wherein the pharmaceutical compound is selected from the group of anti-inflammatory glucocorticoids, immunosuppressive compounds, anti-fungal compounds, antibiotic compounds, anti-viral compounds, and anti-cancer compounds.

In one embodiment of the present invention, there is provided a high dose cyclosporin A (CsA) liposome aerosol composition comprising up to about 30 mg/ml cyclosporin A in up to about 225 mg of a phospholipid/ml starting reservoir concentration.

In another embodiment of the present invention, there is provided a high dose budesonide-liposome (Bud) aerosol composition comprising up to about 15 mg/ml budesonide in up to about 225 mg of a phospholipid/ml starting reservoir concentration.

In a preferred embodiment of the present invention, there is provided a high dose cyclosporin A liposome aerosol composition comprising up to about 20 mg/ml cyclosporin A in up to about 150 mg of dilauroylphosphatidylcholine (DLPC)/ml starting reservoir concentration.

In a most preferred embodiment of the present invention, there is provided a high dose cyclosporin A liposome aerosol composition comprising up to about 21.3 mg/ml cyclosporin A in up to about 160 mg of dilauroylphosphatidylcholine (DLPC)/ml starting reservoir concentration. Other phospholipids might be substituted for DLPC in the high dose the CSA-liposomal formulation.

In another aspect of the present invention, there is provided a high-dose budesonide-liposome aerosol composition comprising up to about 15 mg/ml budesonide in up to about 225 mg of dilauroylphosphatidylcholine(DLPC)/ml starting reservoir concentration.

In still yet a more preferred embodiment of the present invention, there is provided a high-dose budesonide-liposome aerosol composition comprising up to about 12.5 mg/ml budesonide in up to about 200 mg of dilauroylphosphatidylcholine(DLPC)/ml starting reservoir concentration. Other phospholipids might be substituted for DLPC in the high dose the Budesonide-liposomal formulation.

Thus, the present invention provides a high dose anti-inflammatory glucocorticoid-, immunosuppressive compound-, anti-fungal compound-, antibiotic compound-, anti-viral compound-, and anti-cancer compound-liposome aerosol composition comprising about 12–30 mg/ml of the pharmaceutical compound in up to about 130–375 mg of a phospholipid/ml starting reservoir concentration.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention summarized briefly above may be had by reference to certain embodiments which are illustrated in the appended drawings. These drawings form a part of the specification. It is to be noted, however, that the appended drawings illustrate preferred embodiments of the invention and are not to be considered limiting in their scope.

DETAILED DESCRIPTION OF THE INVENTION

Figure 1:
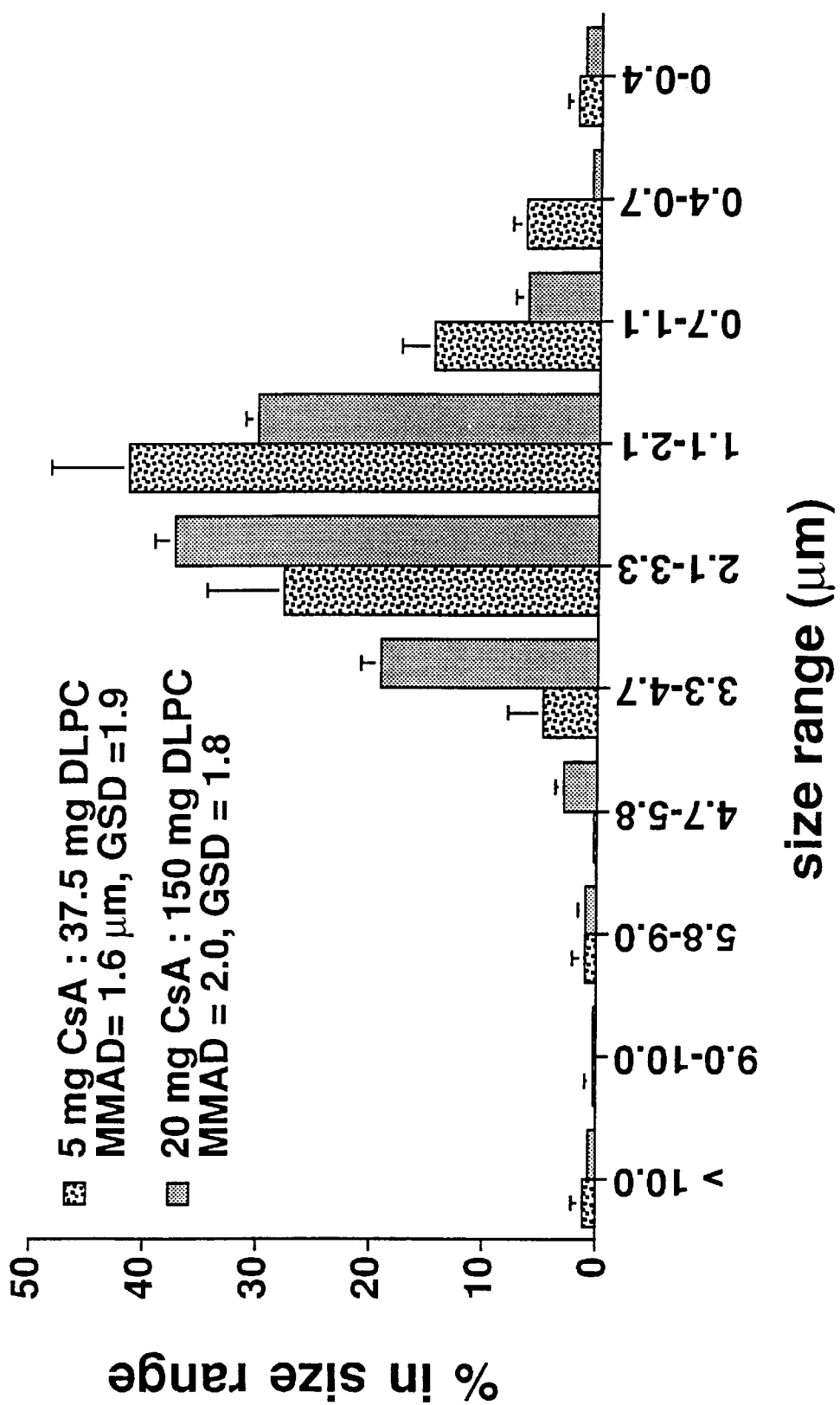
FIG. 1 shows the aerosol distribution profile of high and low dose cyclosporin A-DLPC liposomal formulations nebulized with an Aerotech II nebulizer at a flow rate of 10 liters per minute as determined by the Andersen Cascade Impactor. The data (mean±standard deviation) represent the fractional percentage of total cyclosporin A recovered on each stage of the impactor with associated size cut-off in $\mu$m (n=3 analyses). The mass median aerodynamic diameters (MMAD) and geometric standard deviations (GSD) were calculated on a log-probability plot.

One object of the present invention is to improve the efficiency of delivery of a high dose pharmaceutical compound-liposome aerosol composition. For example, the present invention is drawn to the improved efficiency of delivery of a cyclosporin A-liposome aerosol. In a series of experiments, it was determined that the aerosol drug output could be improved through the utilization of liposomes formulated with low phase transition temperatures, such as DLPC (containing 12 carbon, saturated fatty acid side chains). It was also determined that certain nebulizers increase the aerosol drug-liposome output in the desired size range of 1–3 $\mu$m mass median aerodynamic diameter (MMAD). The cyclosporin A concentration employed in these early studies was 1.0 mg with 7.5 mg DLPC per ml of starting solution in the reservoir.

In 1993, the need to increase the cyclosporin A-liposome aerosol output by scaling up the formulation was recognized. This could be accomplished in different ways, such as selection of a more efficient nebulizer. The cyclosporin A-liposome aerosol output was scaled up through the implementation of the Aerotech II (ATII) nebulizer (from CIS-USA, Bedford, Mass.). The ATII has approximately 50% increased aerosol output over the previously used Puritan Bennett 1600 sj.

A second method of increasing aerosol drug-liposome output was to increase the reservoir concentration of drug and phospholipid in the liquid of the nebulizer reservoir. The cyclosporin A-DLPC liposome concentration of 5 mg cyclosporin A/37.5 mg per ml was successfully increased while achieving desired aerosol output in the range of 1–3 $\mu$m mass median aerodynamic diameter (MMAD). Using a human lung deposition model, analysis of this aerosol indicated that approximately 3.2 mg of cyclosporin A theoretically would deposit within the lung after a single 15 minute inhalation. Studies by the University of Pittsburgh group of lung allograft patients treated with aerosolized cyclosporin A (dissolved in ethanol or propyleneglycol) demonstrated clinical improvement (reversal of graft rejection) when 20 mg of cyclosporin A was delivered to the lung. Using the available cyclosporin A-DLPC liposome system requires approximately 2 hours of aerosol inhalation to deliver this amount. Such a prolonged, daily inhalation interval would likely be cumbersome for the patient, and requires 8 recharges of the nebulizer reservoir. Therefore, the cyclosporin A-DLPC reservoir concentration needed to be increased. However, it is well known in the prior art that it was not possible to nebulize liposomes greater than 50 mg/ml, since greater concentrations resulted in clogging of the nebulizer jets.

The present invention succeeded in achieving 20–30 mg/ml cyclosporin A:150–225 mg DLPC/ml starting reservoir concentration. The particle size was increased marginally by this change, shifting upward the MMAD of the aerosol to 2.0 μm from 1.6 μm as demonstrated with cyclosporin A-DLPC (5 mg/37.5 mg) with no change in the GSD (FIG. 1). The aerosol output of the "high-dose" 20–30 mg cyclosporin A-DLPC significantly was higher than the 5 mg cyclosporin A-DLPC.

Figure 2:
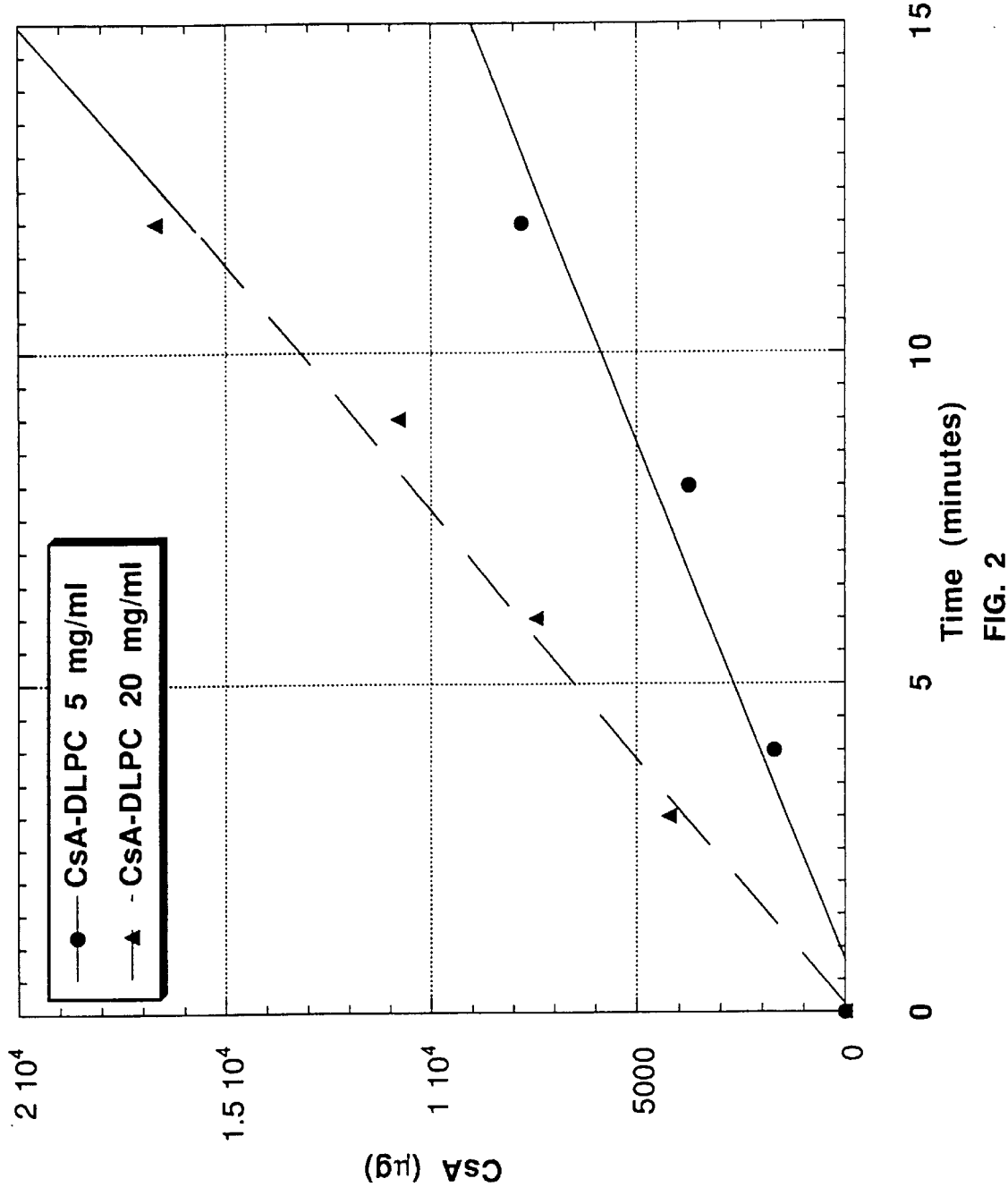
FIG. 2 shows the cyclosporin A inhaled from high and low dose cyclosporin A-DLPC liposomal formulations nebulized with an Aerotech II nebulizer at a flow rate of 10 liters per minute as determined in a human lung simulation model. The values represent cyclosporin A collected at different nebulization times from aerosol samples by filters attached to a Harvard Respirator adjusted to a tidal volume (TV) of 500 ml and a rate of 15 breaths per minute (BPM).

As demonstrated in FIG. 2 in a simulated human lung model, 15 minutes with high-dose cyclosporin A-DLPC, the required time period to deliver a putative therapeutic dose in lung allograft patients would be approximately 45 minutes or less. Certainly, this interval is based on dosing results by other investigators using other cyclosporin A aerosols. Since cyclosporin A-liposomes are theoretically more effective at a lower dose and less toxic than cyclosporin A in ethanol or propylene glycol, the inhalation interval would likely be much less. Increasing the cyclosporin A-DLPC higher than about 30 mg cyclosporin A-225 mg DLPC proved inefficient.

The present invention demonstrated the usefulness of a high dose cyclosporin A-DLPC liposome aerosol in the range of 20–25 mg cyclosporin A/150–200 mg DLPC per ml; although amounts up to 30 mg/ml would also constitute high dose. Other phospholipids might be substituted for DLPC in the high dose cyclosporin A-liposomal formulation. Representative examples of suitable phospholipids include egg yolk phosphatidylcholide, hydrogenated soybean phosphatidylcholide, dimyristoyphosphatidylcholide, diolyeolyl-dipalmitoyleolylphosphatidylcholide and dipalmitoyl phosphatidylcholide.

High dose cyclosporin A-liposome aerosol proves to be useful in a variety of immunologically mediated lung diseases, such as, allograft rejection, bronchiolitis obliterans, allergy, hypersensitivities, and asthma, and proves useful in pediatric, adult, and elderly patients with different nebulizer systems. Different inhalation intervals would be required for treating the various disease entities.

Figure 5:
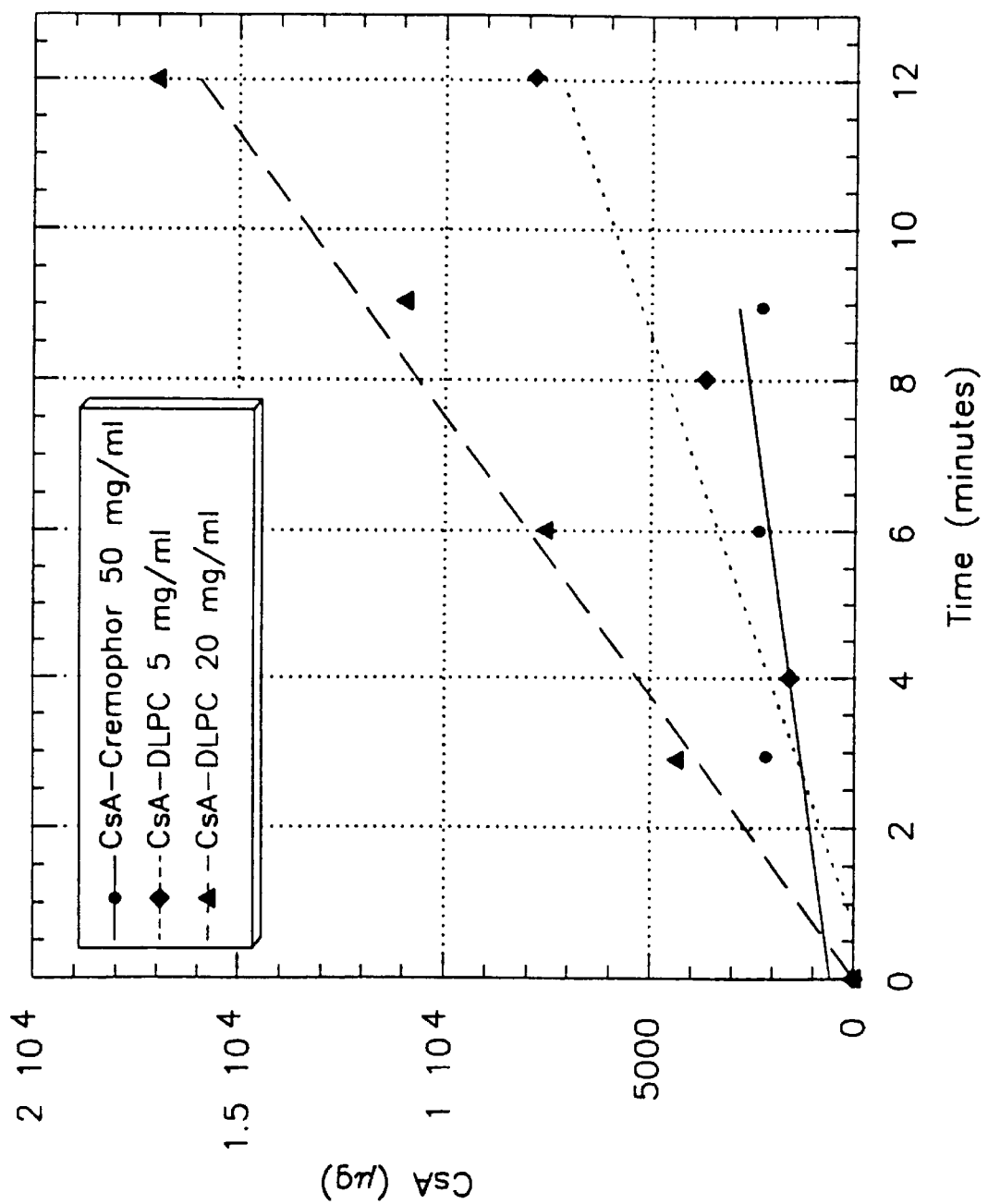
FIG. 5 shows the time frame of simulated CsA concentrations inhaled from nebulized liposomal and cremophor formulations. Plotted are CsA-Cremophor (50 mg/ml; circles), CsA-DLPC (5 mg/ml; filled triangles), and CsA-DLPC (20 mg/ml; diamonds).
Figure 6:
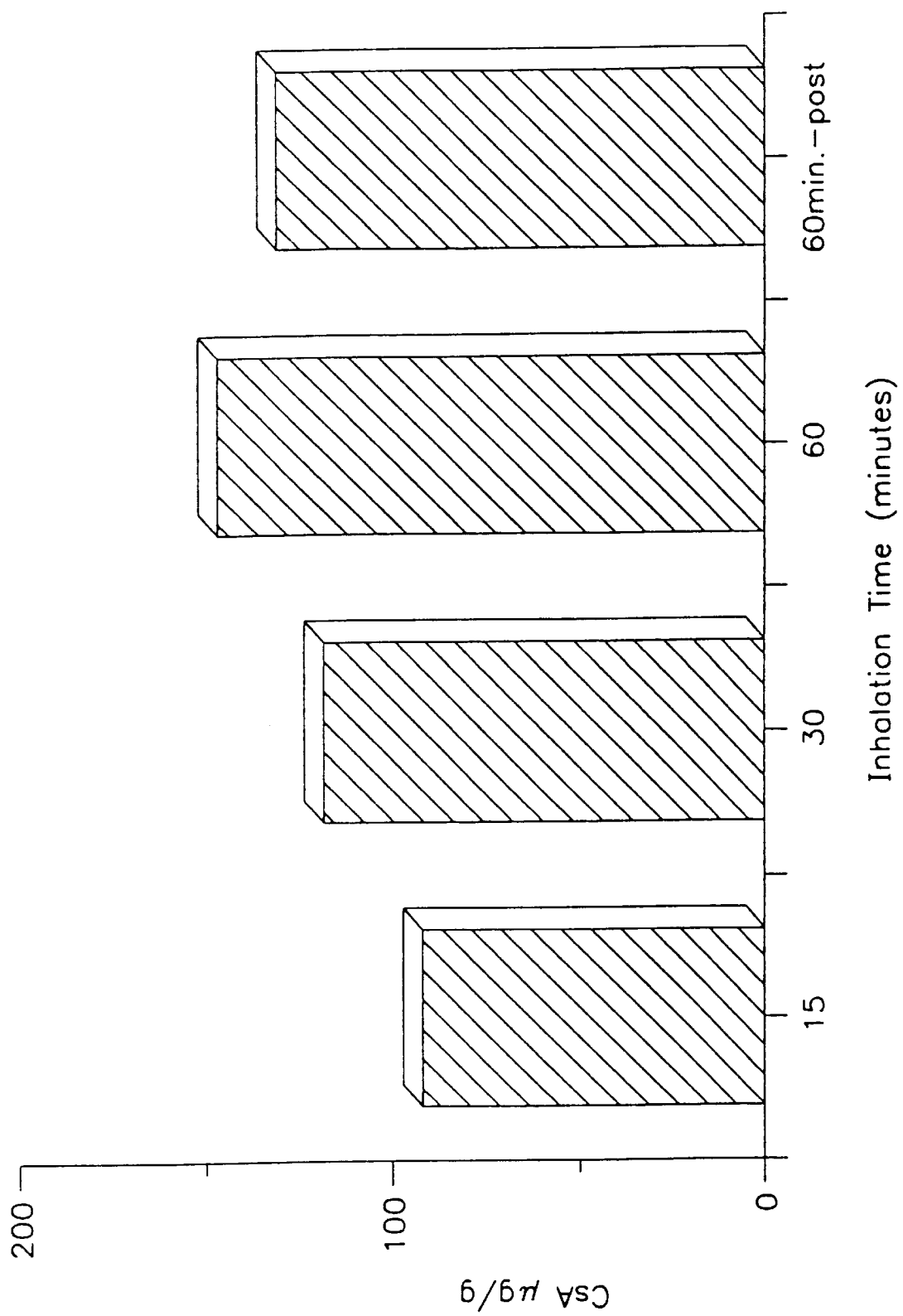
FIG. 6 shows the concentration of pulmonary CsA, over an inhalation time in ICR mice (35 g) after inhalation of nebulized high-dose CsA-DLPC (20 mg/ml).

Producing high dose cyclosporin A-DLPC liposomes are useful since high dose cyclosporin A aerosols are being used to treat lung transplant rejection episodes. In these studies, patients are being treated with nebulized cyclosporin A-cremophor (50 mg cyclosporin A/ml). As demonstrated in the FIG. 5, the aerosol output of cyclosporin A-liposomes (5 mg/ml & 20 mg/ml) is markedly higher. The cyclosporin A-cremophor is very irritating but this aerosol has given some clinical benefit. Thus, the cyclosporin A-liposomes will be even better once tested in similar patients. The cyclosporin A-DLPC liposome aerosol are also effective in the treatment of asthma as described for oral cyclosporin A.

Investigation into the present invention also determined that the glucocorticoid budesonide produces stable liposomes that can be nebulized efficiently and produces aerosols in the range of 1–3 μm MMAD. At this reservoir concentration, the typical inhalation interval required to deliver a daily dose for asthma from the ATII nebulizer would be approximately 15 minutes. This would be clinically feasible and practical to accomplish.

Boehringer-Ingelheim has tested glucocorticoid liposomes in a nebulizer device. The design of their device called for the delivery of 100–200 μg glucocorticoid per 20 μl actuation. A simple math conversion demonstrates that 5,000 to 10,000 μg/ml in the reservoir of the device would be required. In those experiments with the device, Budesonide in an ethanol vehicle was tested.

Based on prior experience, to achieve the necessary concentration with a liposomal formulation, a concentrated and viscous suspension would be produced. In previous experiments with Budesonide, a ratio of 1:25 (Budesonide to DLPC by weight) was employed. Based on the required high DLPC content, various Budesonide-DLPC ratios were examined and the ratio of 1:15 as suitable was identified. The formulation was then scaled up, first to 5 mg Budesonide: 75 mg DLPC per ml and finally to 10 mg Budesonide: 150 mg DLPC per ml. Scaling up with other glucocorticoids (beclomethasone dipropionate or flunisolide) was more difficult due to unstable formulations. The 10 mg Budesonide-150 mg DLPC formulation was stable and could be nebulized with the ATII nebulizer efficiently.

Figure 3:
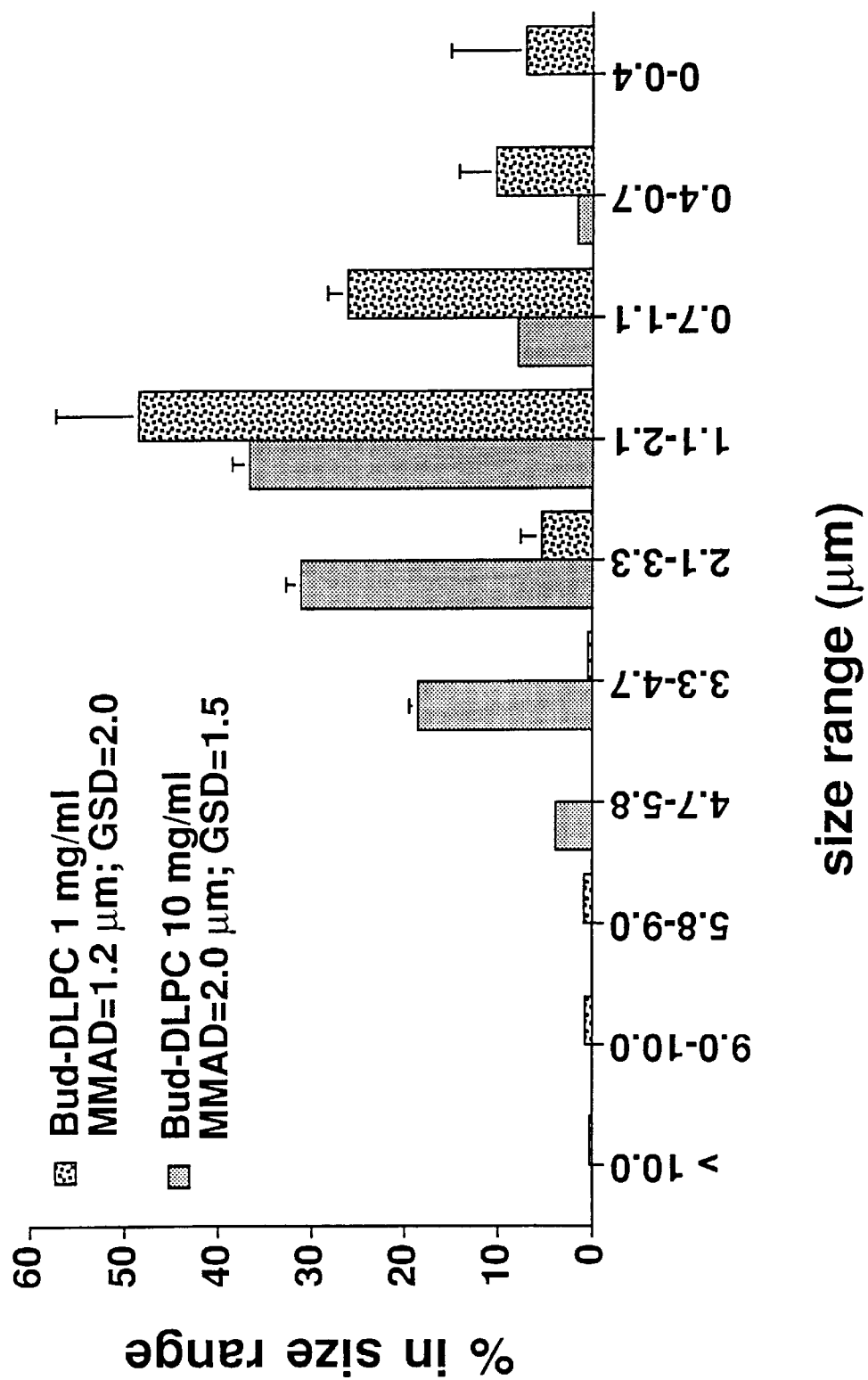
FIG. 3 shows the aerosol distribution profile of high and low dose Budesonide-DLPC liposomal formulations nebulized with an Aerotech II nebulizer at a flow rate of 10 liters per minute as determined by the Andersen Casacade Impactor. The data (mean±standard deviation) represent the fractional percentage of total cyclosporin A recovered on each stage of the impactor with associated size cut-off in $\mu$m (n=3 analyses). The mass median aerodynamic diameters (MMAD) and geometric standard deviations (GSD) were calculated on a log-probability plot.
Figure 4:
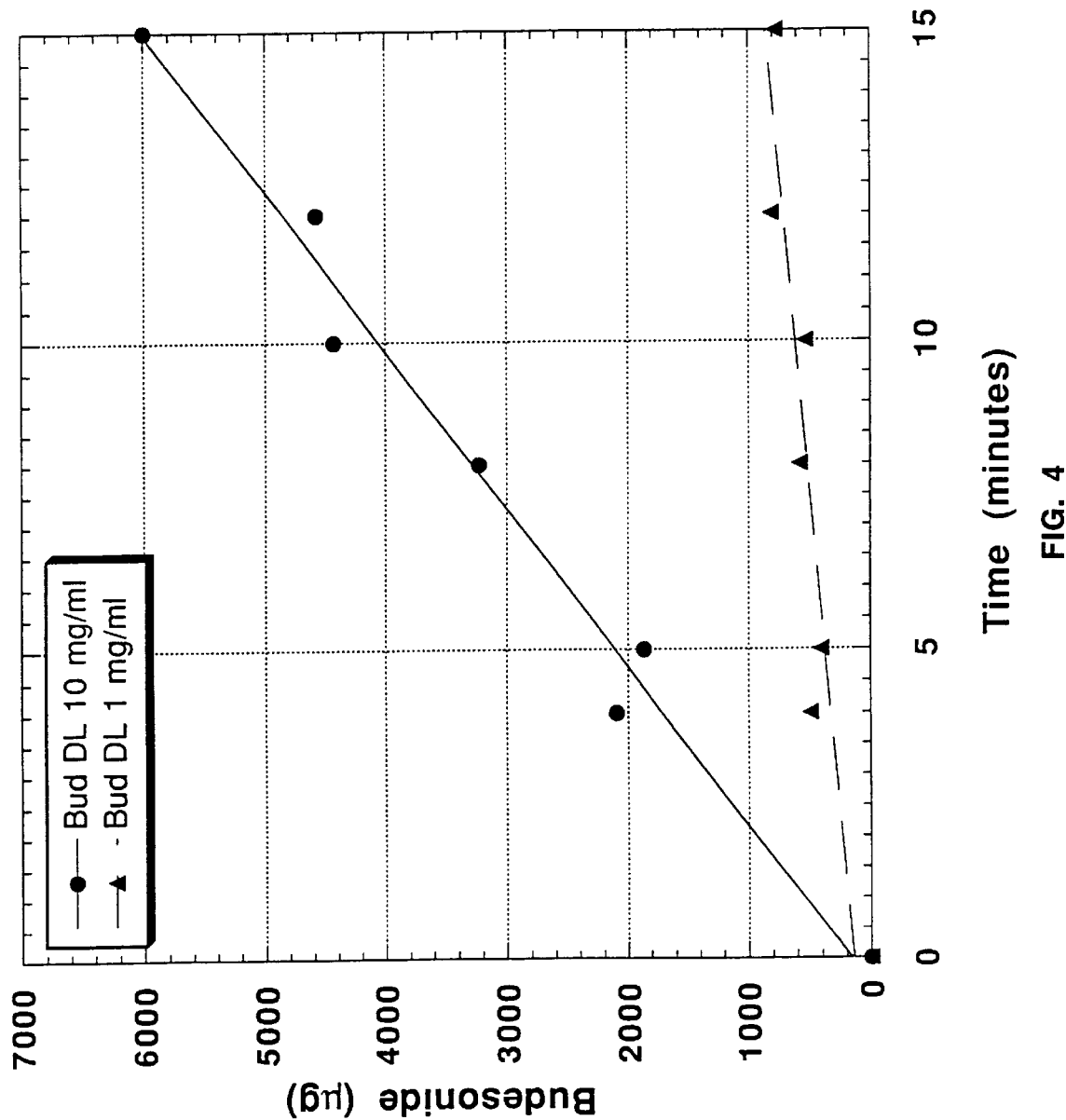
FIG. 4 shows the Budesonide inhaled from high and low dose Budesonide-DLPC liposomal formulations nebulized with an Aerotech II nebulizer at a flow rate of 10 liters per minute as determined in a human lung simulation model with a tidal volume (TV) of 500 ml and 15 breaths per minute (BPM). The values represent Budesonide collected at different nebulization times from aerosol samples by filters attached to a Harvard Respirator adjusted to a tidal volume (TV) of 500 ml and a rate of 15 breaths per minute (BPM).

FIG. 3 demonstrates that increased concentration results in larger aerosol particles increasing the MMAD from 1.2 μm to 2.0 μm with the high dose Budesonide-DLPC. FIG. 4 demonstrates that after a single 15 minute inhalation of this high dose Budesonide-formulation, approximately 6 mg of Budesonide would be inhaled or 6 times the highest clinical daily dose. The relationship between the aerosol output of the low and high dose Budesonide-DLPC is not proportional.

A representative "high dose" Budesonide-DLPC liposome aerosol is in the range of around 12.5 mg Budesonide/ 225 mg DLPC per ml. Other phospholipids might be substituted for DLPC in the high dose Budesonide-liposomal formulation of the present invention. This high dose Budesonide-DLPC liposome aerosol formulation is useful clinically in the treatment of certain inflammatory lung diseases like asthma and interstitial fibrosis, as well as immunologically mediated lung allograft rejection, bronchiolitis obliterans, allergy, and hypersensitivities. This would prove useful in pediatric, adult, and elderly patients with different nebulizer systems.

The following examples are given for the purpose of illustrating various embodiments of the invention and are not meant to limit the present invention in any fashion.

EXAMPLE 1

Liposome Formulation: Preparation of High Dose Drug/ Liposomes

A lyophilization procedure has been developed in the present invention for optimal formulation of various drug/ liposomes. It was ascertained that the optimal cyclosporin A to DLPC ratio was 1:7.5 by weight. To determine the maximum concentration compatible with nebulization, aerosol delivery formulations were produced at 10 to 30 mg cyclosporin A with 75 to 225 mg DLPC, at the optimal CsA to DLPC, ratio of 1:7.5 by weight. It was determined that formulations containing 21.3 mg cyclosporin A: 160 mg DLPC were optimal as judged by aerosol output and particle size for inhalation. For optimized high dose cyclosporin A-liposomes, 100 mg of cyclosporin A (Sandoz Pharmaceuticals or Chemwerth Chemical Company) was mixed with 750 mg of synthetic alpha-lecithin: 1, 2-dilauroyl-sn-glycero-3-phosphocholine (DLPC from Avanti Polar Lipids). Working at 37° C. in a warm room, the drug/DLPC was mixed in 20 ml of tertiary butanol with stirring as described in Waldrep et al., *Int'l J. of Pharmaceutics* 97:205–12 (1993). After mixing, the drug/lipid mixture was pipetted into glass vials, frozen rapidly, then lyophilized overnight to remove the t-butanol leaving a powder mixture.

Multi-lamellar liposomes were produced by adding 10 ml of ultra pure water above the phase transition temperature (Tc) at 25° C. to deliver a final standard drug concentration of 1–30 mg cyclosporin A: 7.5–225 mg DLPC per ml. The mixture was incubated for 30 minutes at room temperature with intermittent mixing to produce multilamellar vesicular liposomes. As an alternative, this liposomal formulation can be prepared by rotary evaporation. Aliquots were taken for determination of drug concentration by HPLC. This simple liposome preparation method was chosen since it can be scaled up easily for large batch preparation.

After swelling, the quality of the liposome preparations was checked for size and for the presence of drug crystals by microscopy using an eye piece, both before and after nebulization. The drug-lipid association (encapsulation efficiency) was determined using percoll gradient analysis as described in O'Riordan, et al., *J. of Aerosol Med.,* in press (1996). Size reduction of the multilamellar vesicular high dose cyclosporin A-DLPC drug-liposome formulations was not needed prior to nebulization since the drug-liposomes (a heterogeneous starting mixture of 2.2 to 11.6 micrometers after swelling) are reduced further in size during nebulization (and continual reflux) by the shear forces generated by extrusion through the jet orifice of the nebulizer. The size range of these liposomes in aerosol droplets is 271–555 nm. Aqueous particles in aerosol contain one to several liposomes. The diameter of the liposomes is smaller than the aqueous aerosol particles in which they are carried (see Waldrep et al., *Int'l J. of Pharmaceutics* 97:205–12 (1993)). After swelling, the formulations are used for nebulization within several hours. Sterile formulations can be kept months at room temperature or in the refrigerator.

Figure 8:
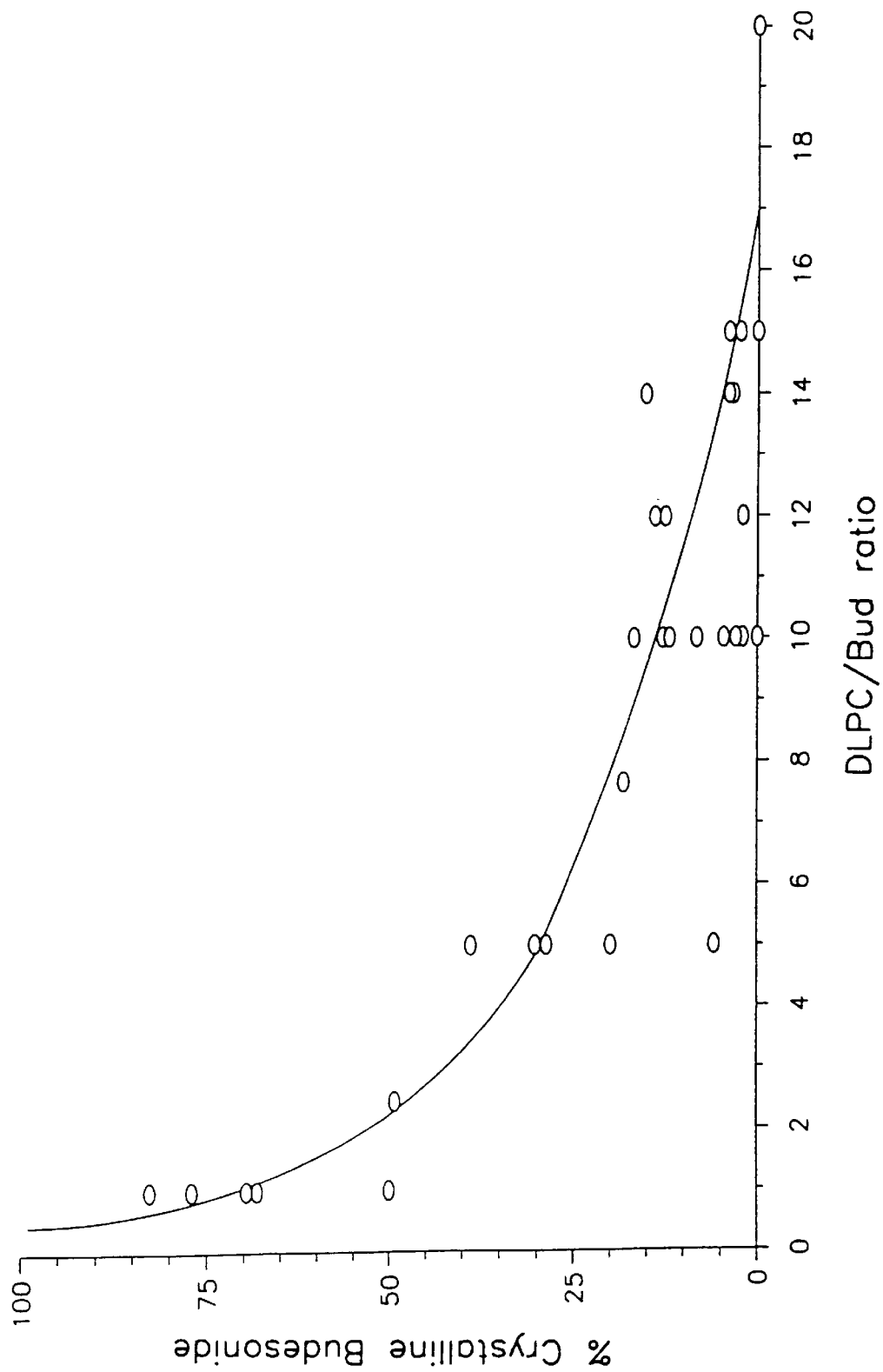
FIG. 8 shows a percoll gradient analysis of Bud-DLPC liposomes.

For formulation of high dose budesonide-DLPC liposomes, the optimal drug to lipid ratio was determined by testing different formulations at Budesonide-DLPC ratios of 1:1 to 1:20. The ratio of 1:15 (by weight) was selected as optimal for the high dose Budesonide-DLPC formulation. The high dose formulation is produced by mixing 10–150 mg of Budesonide with 150–2250 mg of DLPC (as described above for cyclosporin A-DLPC). Working at 37° C. in a warm room, the drug/DLPC was mixed in 20 ml of tertiary butanol with stirring. After mixing, the drug/lipid mixture was pipetted into glass vials, frozen rapidly, then lyophilized overnight to remove the t-butanol, leaving a powder mixture. Multi-lamellar liposomes were produced by adding 10 ml of ultra pure water above the phase transition temperature (Tc) at 25° C. to deliver a final standard drug concentration of 1–15 mg Budesonide: 15–225 mg DLPC per ml of solution. The mixture was incubated for 30 minutes at room temperature with intermittent mixing to produce multilamellar vesicular liposomes. Aliquots were taken for determination of drug concentration by HPLC. As an alternative, this liposomal formulation can be prepared by rotary evaporation. FIG. 8 shows a percoll gradient analysis of Bud-DLPC liposomes (see O'Riordan, et al., *J. of Aerosol Med.,* in press (1996)). Once swollen, the multilamellar vesicular Budesonide-DLPC liposomes were stable for several weeks at room temperature. Sterile preparations were stable for months. Benzalkonium chloride (10 mg/liter) can be added as a preservative.

EXAMPLE 2
Liposome Aerosols: Aerosol Drug-Liposome Treatment

For the generation of drug-liposome aerosols, the Aerotech II nebulizer (CIS-U.S.A., Bedford U.S.A.) was used although other commercial nebulizers could be employed. The ATII is a high-output, efficient nebulizer demonstrated to produce liposome aerosols in the optimal size range of 1–3 gM MMAD for peripheral lung delivery (see Vidgren, et al., *Int'l J. of Pharmaceutics* 115:209–16 (1994). A source of dry air was delivered to the nebulizer and its internal drying air intake via a regulated flow meter was at 10 liters/minute. An initial reservoir volume of 5 ml is sufficient for 15–20 minutes of aerosol. Longer treatment intervals would require refilling the reservoir.

EXAMPLE 3
Drug-liposome Aerosol Particle Distribution

Aerodynamic particle sizing of the drug-liposome aerosols was determined as described in Waldrep et al., *J. of Aerosol Med.* 7:1994 (1994), using an Andersen 1 ACFM non-viable ambient particle sizing sampler (Graseby Andersen Instruments Inc., Atlanta, Ga.) as a simulator of the human lung (Andersen). Drug-liposome aerosols generated from the ATII nebulizer were collected using a vacuum pump (1 ACFM) by impaction on 8 aluminum stages at a standard sampling interval of 0.5 minutes for each experiment. Drug concentrations in aerosol droplets between 0–10 $\mu$m sizes were collected on each stage (0=9.0–10.0 $\mu$m; 1=5.8–9.0 $\mu$m; 2=4.7–5.8 $\mu$m; 3=3.3–4.7 $\mu$m; 4=2.1–3.3 $\mu$m; 5=1.1–2.1 $\mu$m; 6=0.65–1.1 $\mu$m; 7=0.43–0.65 $\mu$m) and determined after elution with 10 ml of ethanol or methanol and HPLC analysis. An USP artificial throat attached to the inlet port of the impactor is used to remove few aerosol particles larger than 10 $\mu$m. The final stage used a glass fiber collection filter. After determination of the drug concentrations for each stage by HPLC, the mass median aerodynamic diameter (MMAD) and geometric standard deviation (GSD) of the drug-liposomes was calculated on a log probability scale with the effective cutoff diameter as the ordinate and the cumulative percent less than the size range (by concentration) as the abscissa (KaleidaGraph 3.0). The MMAD and GSD are determined by the liposomal drug content distributed within the array of droplets comprising the aerosol (see Waldrep et al., *Int'l J. of Pharmaceutics* 97:205–12 (1993)). The droplet array rather than the liposome size determined the MMAD and the GSD. The validity of this method for calculation of MMAD & GSD was verified independently using a Model 3300 TSI Laser Aerosol Particle Sizer.

EXAMPLE 4
Estimation of Inhaled Dosage

For the determination of the estimated inhaled dosage of Bec-DLPC liposome, nebulized samples were collected in a simulated human lung system as described by Smaldone et al., *Am Rev Respir Dis* 143:727–37 (1991). Using a Harvard Respirator, aerosol samples were collected onto Whatman GF/F filters from the ATII nebulizer (10 L/minute flow rate) using 15 breaths per minute with tidal volumes of 500 ml. This basal tidal volume of 500 for males (450 for females) was determined from a nomogram adjusted for breathing frequency, weight, and sex. Aerosol samples were collected over a fifteen minute nebulization interval. The amount of cyclosporin A or Budesonide deposited on the filters was determined after extraction by HPLC analysis.

EXAMPLE 5
Analysis Of Pulmonary Cyclosporin A: Solid Phase Extraction

The following steps were performed:

1. Mouse lung tissue, after inhalation of cyclosporin A-DLPC liposome aerosol, was obtained. An internal CSD standard of 10 $\mu$g (10 $\mu$l of a 1 mg/ml stock) was added. The tissue was homogenized either in a blender or Wig-L-Bug tubes (using 4–5 beads per tube).

2. The homogenized tissue was extracted in 1 ml ultra pure water for 1–2 minutes. These volumes are for one tissue sample and are diluted if more than one tissue sample is pooled.

3. 2 ml of 98% Acetonitrile/2% Methanol and was added and the sample was vortexed.

4. The sample was centrifuged at full speed 20 minutes; and the supernatant was transferred to a clean tube and centrifuged 10 minutes on full speed.

5. The supernatant was collected and 5 ml ultra pure water for every 1 ml used in tissue extraction was added.

6. A Sep-Pak C18 column (Waters Sep-Pak Light for single mouse tissue) was prepared and was washed with 5 ml 95% Ethanol and 5 ml ultra pure water. The sample was added slowly and washed with 5 ml ultra pure water, and 5 ml 50% Acetonitrile 7. The eluate was transferred to a collection tube and eluted with 1 ml Methanol followed by 0.5 ml water.

8. Contaminants were removed by washing the eluate twice with 1.5 ml hexane and discarding the top layer.

9. The extracted eluate was evaporated to dryness using the reacti-vap temperature set on low with minimal air flow.

10. Reconstitution was in 0.3 ml CSA mobile phase and sample on HPLC.

EXAMPLE 6
Drug Analysis By High Pressure Liquid Chromatography (HPLC): Budesonide analysis The HPLC assay was utilized for multiple purposes to determine: the Budesonide content of liposome formulations, the encapsulation efficiency, and the Budesonide content of aerosol samples obtained with the lung simulator. Budesonide concentrations were determined by HPLC analysis using a Waters WISP 717 autosampler and a Waters Nova-Pak C18 (3.9×150 mm) column at room temperature. Peak detection was performed at 238 nanometers using a variable UV/Vis wavelength detector with quantification by a Waters Millenium 2010 Chromatography Manager Version 2.15. The mobile phase utilized for these studies was 50:50 ethanol/water at a flow rate of 0.6 ml per minute (see Andersson & Ryrfeldt, *J Pharm Pharmacol* 36:763–65 (1984)) Samples for analysis were dissolved directly into ethanol (to solubilize the liposomes). Drug standards were prepared from ethanol stocks kept at −80° C.

EXAMPLE 7
Drug Analysis by High Pressure Liquid Chromatography (HPLC):Cyclosporin A Analysis The cyclosporin A in liposomal formulations (to determine cyclosporin A content and encapsulation efficiency) and in aerosol samples was determined by HPLC. A Waters (Milford, Mass.) WISP automatic sample injector and a Supelco LC-1 column heated to 75° C. was used in the assay. The mobile phase was 50% acetonitrile, 20% methanol and 30% water (see Charles et al., *Ther. Drug Monitor.* 10:97–100 (1988)). Peaks were detected at 214 nm using a variable wavelength detector and quantified with the Waters Millenium 2010 Chromatography Manager Version 2.15. Samples for analysis were dissolved directly in methanol (to solubilize the liposomes). Drug standards were prepared from methanol stocks kept at −80° C.

EXAMPLE 8
Drug Analysis By High Pressure Liquid Chromatography (HPLC): DLPC analysis A modification of the HPLC protocol of Grit and Commelin *Chem. & Phys. of Lipids* 62:113–22 (1992), was used. A Waters 717 WISP automatic sample injector and a Sperisorb S5 amino column (25 cm×4.6 mm, 5 $\mu$m) was utilized with acetonitrile, methanol, and 10 mM ammonium/trifluoroacetic acid, pH 4.8 (64:28:8 v:v:v) mobile phase. Peaks were detected with a mass evaporative detector (SEDEX 55, Sedre, France) and quantified with the Waters Millenium 2010 Chromatography Manager Version 2.15. Samples for analysis were dissolved directly in ethanol or methanol (to solubilize the liposomes).

Figure 7:
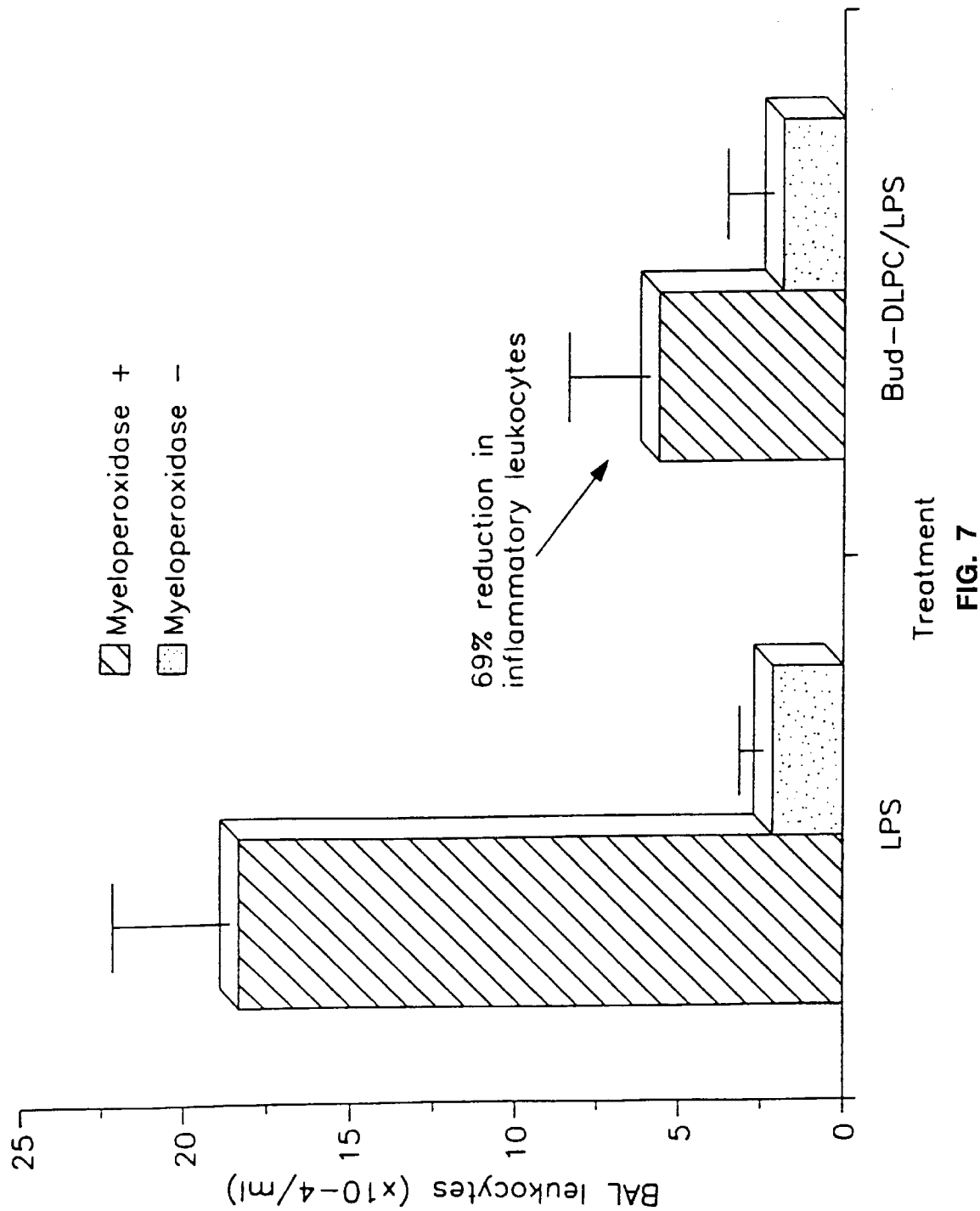
FIG. 7 shows the anti-inflammatory effect of high dose Bud-DLPC on lung bronchiolaralveolar lavage (BAL) leukocytes in response to LPS (endotoxin) challenge.

EXAMPLE 9
Lung Models For Drug Testing In Mice: Acute Inflammation Assay: (LPS) Bronchiolar Lavage Technique Gram negative cell wall lipopolysaccharide (LPS) was used for the reproducible induction of acute pulmonary inflammation in mice. A 10 minute exposure interval to *E. coli* 055:B5 LPS (Sigma) aerosol generated from the PBsj 1600 nebulizer (100 $\mu$g/ml reservoir concentration; 60 ng delivered dose) induced a strong phlogistic response as determined by the accumulation of PMN in the alveoli in response to the elaboration of chemotactic cytokines (detectable at 3 hours; peak response at 6 hours post stimulus). At varied times after exposure to LPS aerosol, the mice were sacrificed by methoxyflurane anesthesia and exsanguinated via the abdominal aorta. The trachea was surgically exposed and canulated with PE50 tubing (outer diameter 0.965 mm, Clay Adams). Using a total volume of 2.0 ml Hank's Balanced Salt Solution (HBSS; Ca/Mg free with EDTA), the lungs are ravaged 5 times with approximately 1.0 ml volume. The yield was typically 85% recovery of lavage fluid. The resulting white cells were counted on a hemocytometer, cytocentrifuged and stained. From the differential count, drug effects were noted by a decrease in the white cell count and by reduced numbers of PMN and/or myeloperoxidase positive cells relative to the resident macrophages and/or myeloperoxidase negative cells. This assay was used as the standard to test drug-lipsome aerosol regimen for biological activity through diminution of the acute inflammatory cellular influx of the airways. FIG. 7 shows the anti-inflammatory effect of high dose Bud-DLPC on lung bronchiolaralveolar lavage (BAL) leukocytes in response to LPS (endotoxin) challenge.

EXAMPLE 10
Cytology: Lung Lavage

The cell preps (lavage, thymocytes, lymph node, or splenocytes) were counted on a hemocytometer, cytocentrifuged onto slides (using the Miles Cyto-Tek), and stained with Wright-Giemsa. May-Grunwald-Giemsa, or leukocyte peroxidase stain depending on the preparation. The differential count was determined by microscopic observation under oil immersion. Biological effects of the drug-liposome aerosol regimen were noted by a decrease in the total white cell count and by reduced numbers of PMN or myeloperoxidase positive cells relative to the resident macrophages.

EXAMPLE 11
Inhibition of Antigen/Mitogen Induced Lymphocyte Blastogenesis in Vitro by CsA Isolated from Mouse Lung Tissues After Aerosol Delivery of CsA-DLPC Liposomes

TABLE 1

| ANTIGEN/MITOGEN | AVERAGE CPM | % INHIBITION |
|---|---|---|
| Media | 2,171 | |
| OVA | 13,640 | |
| OVA + CsA 1 $\mu$g/ml | 2,173 | 99.9 |

TABLE 1-continued

| ANTIGEN/MITOGEN | AVERAGE CPM | % INHIBITION |
|---|---|---|
| Media | 517 | |
| ConA | 24,341 | |
| ConA + CsA 1 µg/ml | 3,041 | 89.4 |

OVA = ovalbumin 250 µg/ml; ConA = concanavlin A 1 µg/ml; CPM = $^3$HTdR counts per minute average of 3.

Biological Activity of CsA Delivered to the Lung by Liposome Aerosol

For testing, a primary immune response was generated within the bronchiolar-associated lymphoid tissues and lung-associated lymph nodes within the mediastinum. After local intranasal immunization of Balb/c mice with alum precipitated ovalbumin (AP-OVA (80 µg) supplemented with *Bordetella pertussis* vaccine), the mice are sacrificed 7 days later, the mediastinum are removed and lymphocytes isolated for in vitro analysis. The proliferation assay consists of alterations in the stimulation of lymphocytes after activation with the sensitizing antigen ovalbumin or with the non-specific T-cell mitogen, Con A plus co-culture with CsA isolated from mouse lung tissues by solid phase extraction and quantified by HPLC. The uptake of $^3$[H]-TdR into DNA was determined at 48–72 hours. Inhibition of specific or non-specific lymphocyte activation was demonstrated by an abolition or reduction in the antigen-specific stimulation or in the inhibition of mitogen responsiveness.

EXAMPLE 12

Physicochemical Analysis:

Surface tension & viscosity:

The surface tension (dynes/cm) was measured using a Tensiomat (Model 21, Fisher Scientific, Indiana, Pa.). A platinum iridium ring of known dimension was raised from the surface of the liquid to be tested under precisely controlled conditions. "Apparent" values read from the instrument were multiplied by a correction factor, F, incorporating dimensions of the measuring ring, density of the liquid, and other variables (according to the manufacturer's instructions). Viscosity measurements were performed using a Gilmont Falling Ball Viscometer (Gilmont Instruments, Barrington, Ill.). The viscosity in centipoises was determined at ambient room temperature.

Size measurements of drug-liposomes:

The particle size of drug liposomal solutions was measured by quasielastic light scattering with a Nicomp Model 370, Submicron Particle Sizer, (Program Version 5.0, Nicomp Particle Sizing Systems, Santa Barbara, Calif.). Drug-liposome samples dispersed in water were analyzed according to the manufacturer's instructions and the data was expressed as intensity weighted vesicle size. Drug-liposome mean particle diameters were measured from reservoir samples initially, after 10 minutes of nebulization, and on aerosol samples recovered using the AGI-4 impinger as described by Waldrep et al., *Int'l J. of Pharmaceutics* 97:205–12 (1993).

Experiments conducted demonstrate that there is increased aerosol output of DLPC liposomes up to 170 mg/ml, with reduction in output at higher concentrations. The aerosol DLPC output (mg/min.) of nebulized empty DLPC, CsA-DLPC, and Bud-DLPC liposomal formulations of increasing concentrations were tested. Aerosols were generated with water tested and standardized Aerotech II nebulizers (initial starting volume of 5 mls; 10 L/min. flow rate) and paired samples were collected in AGI-4 impingers at 4–5 & 6–7 minutes of nebulization. DLPC concentrations were determined by HPLC analysis. Extension of these data to CsA-DLPC liposomes yielded similar results, with maximal liposome aerosol output with 21.3 mg CsA: 160 mg DLPC/ml. For Bud-DLPC liposomes, the maximum aerosol DLPC output was demonstrated with the formulation consisting of 12.5 mg Bud:187.5 mg DLPC/ml. Analysis of nebulizer liquid vehicle discharge demonstrated in concentration dependent, reduced output as determined by the mass aerosolized/minute. Experiments were carried out to determine the mass discharge (gm/min.) of nebulized empty DLPC, CsA-DLPC, and Bud-DLPC liposomal formulations of increasing concentrations. Aerosols were generated with water tested and standardized Aerotech II nebulizers (initial starting volume of 5 mls; 10 L/min. flow rate) and the mass output was determined using an analytical balance after 10 minutes of nebulization.

With increasing liposome concentrations, there are similar concomitant increases in aerosol output up to a critical point (plotted by drug concentration). The aerosol CsA and Bud output (mg/min.) of nebulized CsA-DLPC and Bud-DLPC liposomal formulations of increasing concentrations was determined. Aerosols were generated with water tested and standardized Aerotech II nebulizers (initial starting volume of 5 mls; 10 L/min. flow rate) and paired samples were collected in AGI-4 impingers at 4–5 & 6–7 minutes of nebulization. Drug concentrations were determined by HPLC analysis from aliquots of samples also analyzed for DLPC content (FIG. 1). Measurements of aerosolized drug outputs of CsA and Bud by HPLC analysis demonstrated maximal concentrations for nebulization. For CsA-DLPC liposomes the maximum output was at 21.3 mg CsA: 160 mg/ml. For Bud-DLPC, the maximum was at 12.5 mg Bud: 187.5 mg DLPC. Physicochemical analyses of these liposome formulations demonstrated parallel increases in viscosity (plotted by DLPC concentration). The viscosity (centipoises) analysis of empty DLPC, CsA-DLPC, and Bud-DLPC liposomal formulations of increasing concentrations (initial starting volume 10 mls; ambient room temperature) was determined. The results for DLPC, Bud-DLPC and CsA-DLPC were similar. The viscosities of Bud-DLPC formulations were about 20% less than empty DLPC alone. Viscosities of CsA-DLPC were consistently the lowest and unchanging between 16 mg CsA/120 mg DLPC and 24 mg CsA/180 mg DLPC/ml. These results suggest that for each formulation there is a maximum viscosity compatible with nebulized aerosol output; above this threshold there is no added output with increased drug-liposome concentrations.

Results demonstrate that the addition of CsA and Bud to DLPC liposomes causes a reduction in the formulation surface tension. Surface tension (dynes/cm) analysis of empty DLPC, CsA-DLPC, and Bud-DLPC liposomal formulations of increasing concentrations (initial starting volume 7 mls; ambient room temperature) was determined. The reduction in surface tension was, to a point, concentration dependent, reaching a plateau around 100 mg DLPC/ml. There was no clear association between aerosol output of the liposomal formulations and surface tension. However, with increasing concentration of liposome formulations, there was an inverse relationship noted between surface tension and viscosity measurements.

Analysis of drug-liposome formulations prior to nebulization by quasielastic light scattering demonstrated a heterogeneous starting size range of approximately 2.2 to 11.6 µm (this is at or near the upper accuracy limit of Nicomp 370). After nebulization, there were minimal differences detected among any of the formulations. The size range of liposomes within the nebulizer reservoir were 294 to 502 nm and aerosol samples collected by the AGI-4 impinger ranged from 271 to 555 nm.

High dose formulations of drug-liposomes consisting of 10 mg Bud: 150 mg DLPC and CsA 20 mg: DLPC 150 mg were selected for further aerosol studies. Analysis with the Andersen Cascade Impactor demonstrated values of 2.0 µm MMAD/1.5 GSD for Bud-DLPC and 2.0 µm/1.8 for CsA-DLPC (Table 2). Analysis of these formulations in a simulated human lung model at 15 BPM and 500 ml tidal volume demonstrates that a 3 minute inhalation interval would be required to inhaled a 1,000 µg daily dose of Bud in liposomes, up to 5,000 µg could be inhaled in 12 minutes (Table 2). The results of CsA-DLPC inhalation in the simulated lung model demonstrated that with high dose CsA-DLPC, 4 minutes would be required to inhale 5000 µg nebulized CsA in liposomes; 11.5 minutes would be required to inhale 15,000 µg of CsA (Table 2). These results demonstrate the high capacity of liposomes for aerosol drug delivery.

TABLE 2

Aerosol analysis and inhaled concentrations of nebulized high dose Bud-DLPC and CsA-DLPC liposomal formulations.

| Bud 10 mg-DLPC 150 mg | 1,000 µg dose | 5,000 µg dose |
|---|---|---|
| 2.0 µm MMAD*<br>1.5 GSD | 3 minute<br>inhalation# | 12 minute<br>inhalation# |
| CsA 20 mg-DLPC 150 mg | 5,000 µg dose | 15,000 µg dose |
| 2.0 µm MMAD*<br>1.8 GSD | 4 minute<br>inhalation# | 11.5 minute<br>inhalation# |

*Andersen Cascade Impactor (mean of 3 determinations). #Human lung simulation Model (15BPM/500 ml TV) dosage calculated by linear regression analysis (Bud-DLPC n = 3; CsA-DLPC n = 2 analyses).

The present invention is directed to a high dose cyclosporin A liposome aerosol composition comprising up to about 30 mg/ml cyclosporin A in up to about 225 mg of a phospholipid/ml starting reservoir concentration. Preferably, the liposome aerosol composition comprises up to about 21.3 mg/ml cyclosporin A in up to about 160 mg of a phospholipid/ml starting reservoir concentration. Generally, in the cyclosporin A liposome aerosol composition of the present invention, the particle size as measured by the mass median aerodynamic diameter is in the range of from about 1.0 µm to about 3.0 µm. Further, in the cyclosporin A liposome aerosol composition, the ratio of cyclosporin A to phospholipid is from about 1 to about 7.5. Preferably, the phospholipid is selected from the group consisting of egg yolk phosphatidylcholide, hydrogenated soybean phosphatidylcholide, dimyristoyphosphatidylcholide, diolyeolyl-dipalmitoyleolyl phosphatidylcholide and dipalmitoyl phosphatidylcholide. In general, the cyclosporin A liposome aerosol composition of the present invention may be used to treat an immunologically mediated lung disease. Preferably, such an immunologically mediated lung disease is selected from the group consisting of allograft rejection, bronchiolitis obliterans, allergy, hypersensitivities and asthma.

The present invention is also directed to a high dose budesonide-liposome aerosol composition comprising up to about 15 mg/ml budesonide in up to about 225 mg of a phospholipid/ml starting reservoir concentration. Most preferably, the high dose budesonide-liposome aerosol composition comprises up to about 15 mg/ml budesonide in up to about 225 mg of a phospholipid/ml starting reservoir concentration. For the budesonide-liposome aerosol composition of the present invention, the particle size as measured by the mass median aerodynamic diameter is in the range of from about 1.0 µm to about 2.0 µm. Generally, the budesonide-liposome aerosol composition has a ratio of budesonide to phospholipid is from about 1 to about 15. Representative examples of phospholipid are given above. Typically, the budesonide-liposome aerosol composition may be used to treat immunologically mediated and inflammatory lung diseases. Representative examples of immunologically mediated and inflammatory lung diseases are given above. Cyclosporin A indirectly inhibits inflammation by blocking the immune response. Budesonide inhibits both immune responses and inflammation. These lung diseases can have both components.

The present invention is directed further to a method of treating an individual having an immunologically mediated lung disease, comprising the step of administering to said individual a pharmacologically acceptable dose of a high dose cyclosporin A liposome aerosol composition. The present invention is further directed to a method of treating an individual having an immunologically mediated lung disease, comprising the step of administering to said individual a pharmacologically acceptable dose of a high dose budesonide liposome aerosol composition. Preparation of suitable pharmaceutical compositions and concentrations for administration will be readily apparent to those having ordinary skill in this art given the teachings herein.

The present invention is also directed to a high dose cyclosporin A liposome aerosol composition comprising up to about 30 mg/ml cyclosporin A in up to about 225 mg of dilauroylphosphatidylcholine/ml starting reservoir concentration. Further provided is a high dose budesonide-liposome aerosol composition comprising up to about 15 mg/ml budesonide in up to about 225 mg of dilauroylphosphatidylcholine/ml starting reservoir concentration.

The present invention is drawn in general to a high dose pharmaceutical liposome aerosol composition comprising about 12–30 mg/ml of a pharmaceutical compound, and about 130–375 mg of a phospholipid/ml starting reservoir concentration. For example, the present invention is drawn to anti-inflammatory glucocorticoids, immunosuppressive compounds, anti-fungal compounds, antibiotic compounds, anti-viral compounds, and anti-cancer compounds delivered via a high dose liposome aerosol composition in a phospholipid.

Any patents or publications mentioned in this specification are indicative of the levels of those skilled in the art to which the invention pertains. These patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those inherent in the disclosure. The present examples along with the methods, procedures, treatments, molecules, and specific compounds described are presently representative of preferred embodiments, are exemplary, and are not intended as limitations on the scope of the invention. Changes to these methods and other uses which are encompassed within the spirit of the invention as defined by the scope of the claims will occur to those skilled in the art.

What is claimed is:

1. A high dose cyclosporin A liposome aerosol composition comprising about 5 mg/ml to about 30 mg/ml cyclosporin A and about 37.5 mg to about 225 mg of a phospholipid/ml starting reservoir concentration.

2. The cyclosporin A liposome aerosol composition of claim 1, comprising about 5 mg/ml to about 21.3 mg/ml cyclosporin A and about 37.5 mg to about 160 mg of a phospholipid/ml starting reservoir concentration.

3. The cyclosporin A lipsome aerosol composition of claim 1, wherein a particle size of said liposome as measured by mass median aerodynamic diameter is in the range of from about 1.0 μm to about 3.0 μm.

4. The cyclosporin A liposome aerosol composition of claim 1, wherein the ratio of cyclosporin A to phospholipid is from about 1 to about 7.5.

5. The cyclosporin A liposome aerosol composition of claim 1, wherein the phospholipid is selected from the group consisting of egg yolk phosphatidylcholide, hydrogenated soybean phosphatidylcholide, dimyristoyphosphatidylcholide, dilauroylphosphatylcholine, diolyeolyl-dipalmitoyleolylphosphatidylcholide and dipalmitoyl phosphatidylcholide.

6. The cyclosporin A liposome aerosol composition of claim 1, wherein the composition is used to treat an immunologically mediated lung disease.

7. The cyclosporin A liposome aerosol composition of claim 1, wherein said immunologically mediated lung disease is selected from the group consisting of allograft rejection, bronchiolitis obliterans, allergy, hypersensitivities and asthma.

8. A high dose budesonide-liposome aerosol composition comprising about 1 mg/ml to about 15 mg/ml budesonide in about 15 mg to about 225 mg of a phospholipid/ml starting reservoir concentration, wherein a particle size of said liposome as measured by mass median aerodynamic diameter is in the range of from about 1.0 μm to about 3.0 μm.

9. The budesonide-liposome aerosol composition of claim 8 comprising about 1 mg/ml to about 12.5 mg/ml budesonide in about 15 mg to about 187.5 mg of a phospholipid/ml starting reservoir concentration.

10. The budesonide-liposome aerosol composition of claim 8, wherein the ratio of budesonide to phospholipid is from about 1 to about 15.

11. The budesonide-liposome aerosol composition of claim 8, wherein the phospholipid is selected from the group consisting of egg yolk phosphatidylcholide, hydrogenated soybean phosphatidylcholide, dilauroylphosphatylcholine, dimyristoyphophatidylcholide, diolyeolydipalmitoyleolylphosphatidylcholide and dipalmitoyl phosphatidylcholide.

12. The budesonide-liposome aerosol composition of claim 8, wherein the composition is used to treat an immunologically mediated and inflammatory lung disease.

13. The budesonide-liposome aerosol composition of claim 12, wherein said immunologically mediated and inflammatory lung disease is selected from the group consisting of allograft rejection, bronchiolitis obliterans, allergy, hypersensitivities and asthma.

14. A high dose cyclosporin A liposome aerosol composition comprising about 5 mg/ml to about 21.3 mg/ml cyclosporin A in about 37.5 mg to about 160 mg of dilauroylphosphatidylcholine/ml starting reservoir concentration.

15. A high dose budesonide-liposome aerosol composition comprising about 1 mg/ml to about 12.5 mg/ml budesonide in about 15 mg to about 187.5 mg of dilauroylphosphatidylcholine/ml starting reservoir concentration, wherein a particle size of said liposome as measured by mass median aerodynamic diameter is in the range of from about 1.0 μm to about 3.0 μm.

\* \* \* \* \*

UNITED STATES PATENT AND TRADEMARK OFFICE
CERTIFICATE OF CORRECTION

PATENT NO. : 5,958,378
DATED : September 28, 1999
INVENTOR(S) : J. Clifford Waldrep, et al It is certified that error appears in the above-identified patent and that said Letters Patent is hereby corrected as shown below:

In Column 3, line 10, "Budesonide-liposomal" should read --budesonide-liposomal--.

In Column 3, line 63, "Budesonide" should read --budesonide--.

In Column 3, line 64, "Budesonide" should read --budesonide--.

In Column 4, line 1, "Budesonide" should read --budesonide--.

In Column 4, line 15, "Bud-DLPC" should read --bud-DLPC--.

In Column 4, line 17, "Bud-DLPC" should read --bud-DLPC--.

In Column 6, line 8, "Budesonide" should read --budesonide--.

In Column 6, line 10, "Budesonide" should read --budesonide--.

UNITED STATES PATENT AND TRADEMARK OFFICE
CERTIFICATE OF CORRECTION

PATENT NO. : 5,958,378
DATED : September 28, 1999
INVENTOR(S) : J. Clifford Waldrep, et al It is certified that error appears in the above-identified patent and that said Letters Patent is hereby corrected as shown below:

In Column 6, lines 12-13, "Budesonide" should read --budesonide--.

In Column 6, line 13, "Budesonide" should read --budesonide--.

In Column 6, line 16, "Budesonide" should read --budesonide--.

In Column 6, line 21, "Budesonide" should read --budesonide--.

In Column 6, line 23, "Budesonide" should read --budesonide--.

In Column 6, line 24, "Budesonide" should read --budesonide--.

In Column 6, line 26, "Budesonide" should read --budesonide--.

In Column 6, line 28, "Budesonide" should read --budesonide--.

In Column 6, line 29, "Budesonide" should read --budesonide--.

UNITED STATES PATENT AND TRADEMARK OFFICE
CERTIFICATE OF CORRECTION

PATENT NO. : 5,958,378
DATED : September 28, 1999
INVENTOR(S) : J. Clifford Waldrep, et al It is certified that error appears in the above-identified patent and that said Letters Patent is hereby corrected as shown below:

In Column 6, line 31, "Budesonide" should read --budesonide--.

In Column 6, line 33, "Budesonide" should read --budesonide--.

In Column 7, line 34, "Budesonide" should read --budesonide--.

In Column 7, line 36, "Budesonide" should read --budesonide--.

In Column 7, line 38, "Budesonide" should read --budesonide--.

In Column 7, line 47, "Budesonide" should read --budesonide--.

In Column 7, line 54, "Bud-DLPC" should read --bud-DLPC--.

In Column 7, line 56, "Budesonide" should read --budesonide--.

UNITED STATES PATENT AND TRADEMARK OFFICE
CERTIFICATE OF CORRECTION

PATENT NO. : 5,958,378
DATED : September 28, 1999
INVENTOR(S) : J. Clifford Waldrep, et al It is certified that error appears in the above-identified patent and that said Letters Patent is hereby corrected as shown below:

In Column 8, line 48, "*Am Rev Respir Dis*" should read --*Am. Rev. Respir. Dis.*--.

In Column 8, line 56, "Budesonide" should read --budesonide--.

In Column 9, line 5, please delete the word "and".

In Column 9, line 29, "Budesonide" should read --budesonide--.

In Column 9, line 30, "Budesonide" should read --budesonide--.

In Column 9, line 40, "*J Pharm Pharmacol*" should read --*J. Pharm. Pharmacol.*--.

In Column 9, line 52, please delete the word "was".

In Column 10, line 1, "was" should read --were--.

In Column 10, line 28, "ravaged" should read --lavaged--.

UNITED STATES PATENT AND TRADEMARK OFFICE
CERTIFICATE OF CORRECTION

PATENT NO. : 5,958,378
DATED : September 28, 1999
INVENTOR(S) : J. Clifford Waldrep, et al It is certified that error appears in the above-identified patent and that said Letters Patent is hereby corrected as shown below:

In Column 10, line 49, please insert a comma after "stain".

In Column 11, line 48, please delete the period after "Sizer."

In Column 11, line 62, "Bud-DLPC" should read --bud-DLPC--.

In Column 12, line 4, "Bud-DLPC" should read --bud-DLPC--.

In Column 12, line 6, "Bud" should read --bud--.

In Column 12, line 20, "Bud" should read --bud--.

In Column 12, line 29, "Bud" should read --bud--.

In Column 12, line 31, "Bud" should read --bud--.

In Column 12, line 37, "Bud" should read --bud--.

In Column 12, line 41, "Bud" should read --bud--.

In Column 12, line 49, "Bud" should read --bud--.

UNITED STATES PATENT AND TRADEMARK OFFICE
CERTIFICATE OF CORRECTION

PATENT NO. : 5,958,378
DATED : September 28, 1999
INVENTOR(S) : J. Clifford Waldrep, et al It is certified that error appears in the above-identified patent and that said Letters Patent is hereby corrected as shown below:

In Column 12, line 52, "Bud-DLPC" should read --bud-DLPC--.

In Column 13, line 5, "Bud" should read --bud--.

In Column 13, line 8, "Bud-DLPC" should read --bud-DLPC--.

In Column 13, line 12, "Bud" should read --bud--.

In Column 13, in the footnote under Table 2, line 36, "Bud-DLPC" should read --bud-DLPC--.

Signed and Sealed this

Twenty-fourth Day of April, 2001

Attest:

NICHOLAS P. GODICI

*Attesting Officer*   *Acting Director of the United States Patent and Trademark Office*